(12) United States Patent
Cockett et al.

(10) Patent No.: US 6,306,591 B1
(45) Date of Patent: Oct. 23, 2001

(54) SCREENING FOR THE MOLECULAR DEFECT CAUSING SPIDER LAMB SYNDROME IN SHEEP

(75) Inventors: Noelle E. Cockett, Mendon, UT (US); Jonathan E. Beever, Monticello, IL (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 09/099,749

(22) Filed: Jun. 18, 1998

Related U.S. Application Data

(60) Provisional application No. 60/050,127, filed on Jun. 18, 1997.

(51) Int. Cl.⁷ .............................. C12Q 1/68; C12P 19/34; G01N 33/00; C07H 21/02; C07H 21/04
(52) U.S. Cl. .................... 435/6; 435/91.1; 435/91.2; 436/94; 536/23.1; 536/24.3; 536/24.33
(58) Field of Search ................ 435/6, 91.1, 91.2, 435/183; 536/23.1, 24.3, 24.33, 25.3; 436/94

(56) References Cited

U.S. PATENT DOCUMENTS 5,358,649  10/1994  MacLennan et al. .................... 435/6

OTHER PUBLICATIONS

Cockett et al., Localization of the locus causing Spider Lamb Syndrome to the distal end of ovine chromosome 6. Mammal. Genome 10, 35–38, 1999.*

Lee et al., Linkage of Marfan syndrome and a phenotypically related disorder to two different fibrillin genes. Nature 352, 330–334, 1991.*

Suzuki et al., Amion acid sequence of a novel integrin beta 4 subunit and primary expression of the mRNA in epithelial cells. EMBO J. 9, 757–763, 1990.*

Bellus et al., A recurrent mutation in the tyrosine kinase domain of fibroblast growth factor receptor 3 causes hypochondroplasia. Nature Genetics 10, 357–359. 1995.*

Rousseau et al., Mutation in the gene encoding fibroblast growth factor receptor–3 in achondroplasia. Nature 371, 252–254, 1994.*

Sambrook et al., Molecular Cloning: A Laboratory Manual, 2nd Edition, p. 11.7, 1989. Published by Cold Spring Harbor Laboratory Press.*

Stratagene Catalog (1988), p. 39. Published by Stratagene, 11011 North Torrey Pines Road, La Jolla, CA 92037.*

Baron et al., "Induction of Growth Plate Cartilage Ossification by Basic Fibroblast Growth Factor", *Endocrinology*, vol. 135, No. 6, 1994, pp. 2790–2793.

Beever et al., "Polymorphism identification in the ACADM, AT3, IL10, MYOG and TSHB genes of cattle", *International Society for Animal Genetics,* Animal Genetics 28, Jun. 2, 1997, pp. 373–376.

(List continued on next page.)

*Primary Examiner*—Ethan Whizanant
*Assistant Examiner*—Frank Lu
(74) *Attorney, Agent, or Firm*—Clayton, Howarth & Cannon, P.C.

(57) ABSTRACT

The present invention relates to the field of sheep genetics. Specifically, it relates to materials and methods used to detect a recessive gene causative for hereditary chondroplasia or "Spider Lamb Syndrome". Disclosed are genetic markers for Spider Lamb Syndrome and methods for screening sheep to differentiate those that possess no, one, or two copies of the Spider lamb Syndrome defective gene. In addition, methods are described for identifying other markers associated with Spider Lamb Syndrome. The markers are based upon the presence or absence of certain polymorphisms in the ovine fibroblast growth factor receptor 3 gene. Preferably, the polymorphisms are detected as polymerase chain reaction-restriction fragment length polymorphisms or single strand conformational polymorphisms.

17 Claims, 4 Drawing Sheets

OTHER PUBLICATIONS

Bellus et al., "A recurrent mutation in the tyrosine kinase domain of fibroblast growth factor receptor 3 causes hypochondroplasia", *Nature Genetics*, vol. 10, Jul. 1995, pp. 357–359.

Berg et al., "The Mode of Inheritance of the "Spider" Lamb Syndrome in Suffolk Sheep", *Sid Research Digest*, Fall 1987, pp. 1–3.

Bishop et al., "A Genetic Linkage Map for Cattle", *Genetics*, 136, Feb., 1994, pp. 619–639.

Broad et al., "Progress in mapping the sheep genome: new chromosomal assignments and SheepBase upgraded", *1996 International Society for Animal Genetics*, Animal Genetics 27 (Suppl.2), pp. 85–86.

Cai et al., "Construction and Characterization of a Bovine Bacterial Artificial Chromosome Library", *Genomics 28*, 1995, pp. 001–0014.

Chellaiah et al., "Fibroblast Growth Factor Receptor (FGFR) 3", *The Journal of Biological Chemistry*, vol. 269, No. 15, 1994, pp. 11620–11627.

Colvin et al., "Skeletal overgrowth and deafness in mice lacking fibroblast growth factor receptor 3", *Nature Genetics*, vol. 12, Apr. 12, 1996, pp. 390–397.

Crawford et al., "An Autosomal Genetic Linkage Map of the Sheep Genome", *Genetics 140*, Jun. 1995, pp. 703–724.

Deng et al., "Fibroblast Growth Factor Receptor 3 Is a Negative Regulator of Bone Growth", *Cell*, vol. 84, Mar. 22, 1996, pp. 911–921.

Gusella et al., "Deletion of Huntington's disease–linked G8 (D4S10) locus in Wolf–Hirschhorn syndrome", *Nature*, vol. 318, Nov. 7, 1985, pp. 75–78.

Hulme et al., "Polymorphic sheep microsatellites at the McM2, McM131, McM135, McM136, McM140, McM200, McM214, McM373, McM505, McM507 and McM512 loci", *Animal Genetics 26*, pp. 369–370.

Kappes et al., "A Second–Generation Linkage Map of the Bovine Genome", *Genome Research*, 1996, pp. 235–249.

Kato et al., "Fibroblast Growth Factor Is an Inhibitor of Chondrocyte Terminal Differentiation", *The Journal of Biological Chemistry*, vol. 265, No. 10, Apr. 5, 1990, pp. 5903–5909.

Keegan et al., "Isolation of an additional member of the fibroblast growth factor receptor family, FGFR–3", *Proc. Natl. Acad. Sci. USA*, vol. 88, Feb. 1991, pp. 1095–1099.

Lumsden et al., "Characterization and linkage mapping of ten sheep microsatellite markers derived from a sheep X hamster cell hybrid", *Animal Genetics*, 27, 1996, pp. 203–206.

Miller et al., "A simple salting out procedure for extracting DNA from human nucleated cells", *Nucleic Acids Research*, vol. 16, No. 3, 1988, p. 1215.

Mohammadi et al., "Identification of Six Novel Autophosphorylation Sites on Fibroblast Growth Factor Receptor 1 and Elucidation of Their Importance in Receptor Activation and Signal Transduction", *Molecular and Cellular Biology*, Mar. 1996, pp. 977–989.

Naski et al., "Graded activation of fibroblast growth factor receptor 3 by mutations causing achondroplasia and thanatophoric dysplasia", *Nature Genetics*, vol. 13, Jun. 1996, pp. 233–237.

Ornitz et al., "Ligand Specificity and Heparin Dependence of Fibroblast Growth Factor Receptors 1 and 3", *The Journal of Biological Chemistry*, vol. 267, No. 23, Aug. 15, 1992, pp. 16305–16311.

Perez–Castro et al., "Genomic Organization of the Mouse Fibroblast Growth Factor Receptor 3 (Fgfr3) Gene", *Genomics 30*, 1995, pp. 157–162.

Peters et al., "Unique Expression Pattern of the FGF Receptor 3 Gene during Mouse Organogenesis", *Developmental Biology 155*, 1993, pp. 423–430.

Phillips et al., "Ovine hereditary chondrodysplasia (spider syndrome) in Suffolk lambs", *Australian Veterinary Journal*, vol. 70, No. 2, Feb. 1992, pp. 73–74.

Polymeropoulos et al., "The Gene for the Ellis–van Creveld Syndrome Is Located on Chromosome 4p16", *Genomics 35*, Article No. 0315, 1996, pp. 1–5.

Rook et al., "Diagnosis of hereditary chondrodysplasia (spider lamb syndrome) in sheep", *JAVMA*, vol. 193, No. 6, Sep. 15, 1988, pp. 713–718.

Saperstein et al., "Congential Defects of Sheep", *JAVMA*, vol. 167, 1975, pp. 314–322.

Shiang et al., "Mutations in the Transmembrane Domain of FGFR3 Cause the Most Common Genetic Form of Dwarfism, Achondroplasia", *Cell*, vol., 78, Jul. 29, 1994, pp. 335–342.

Su et al., "Activation of Stat1 by mutant fibroblast growth–factor receptor in thanatophoric dysplasia type II dwarfism", *Nature*, vol. 386/20, Mar. 1997, pp. 288–292.

Tavormina et al., "Thanatophoric dysplasia (types I and II) caused by distinct mutations in fibroblast growth factor receptor 3", *Nature Genetics*, vol. 9, Mar. 1995, pp. 321–328.

Teres et al., "Molecular Genetic Markers", *Animal Genetics*, 27, 1996, p. 371.

Thomas et al., "Research: Spider Syndrome Other Genetic Defects", *Sheep Magazine*, 7(8), 1986, pp. 44–46.

Thomas et al., "Spider Syndrome—A Genetic Defect Found in American Suffolk Sheep", *3rd World Congress on Sheep and Beef Cattle Breeding*, vol. 1, 1988, pp. 649–651.

Thompson et al., "A Gene Encoding a Fibroblast Growth Factor Receptor Isolated from the Huntington Disease Gene Region of Human Chromosome 4", *Genomics 11*, 1991, pp. 1133–1142.

Troyer et al., "A Morphologic and Biochemical Evaluation of the Spider Syndrome in Suffolk Sheep", *Anat. Histol. Embryol. 17*, 1988, pp. 289–300.

Vanek et al., "Comparing spider syndrome in Hampshire and Suffolk sheep", *Veterinary Medicine*, Apr. 1987, pp. 430–437.

Vanek et al., "Comparison of G–banded chromosomes from clinically normal lambs and labms affected with ovine hereditary chondrodysplasia (spider syndrome)", *Am. J. Vet. Res.*, vol. 49, No. 7, Jul. 1988, pp. 1164–1168.

Vanek et al., "Radiographic diagnosis of hereditary chondrodysplasia in newborn lambs", *JAVMA*, vol. 194, No. 2, Jan. 15, 1989, pp. 244–248.

Vanek et al., "Spider syndrome in lambs: A clinical and postmortem analysis", *Veterinary Medicine*, Jul. 1986, pp. 663. 665.

Wang et al., "Simulated Effects of Reproductive Performance On Life–Cycle Efficiency of Lamb and Wool Production at Three Lambing Intervals", *J. Anim. Sci.*, 1991, pp. 4338–4347.

Wang et al., "A Natural Kinase–Deficient Variant of Fibroblast Growth Factor Receptor 1", *Biochemistry*, vol. 35, No. 31, 1996, pp. 10134–10142.

Weber et al., "Genomic organization and complete sequence of the human gene encoding the β–subunit of the cGMP phosphodiesterase and its localisation to 4p16.3", *Nucleic Acids Research*, vol. 19, No. 22, 1991, pp. 6263–6268.

Web Site printout, "#100800 Achondroplasia; ACH", 17 pages.

Web Site printout, "134934 Fibroblast Growth Factor Receptor–3; FGFR3", 10 pages.

Webster et al., "Constitutive activation of fibroblast growth factor receptor 3 by the transmembrane domain point mutation found in achondroplasia", *The EMBO Journal*, vol. 15, No. 3, 1996, pp. 520–527.

Webster et al., "FGFR activation in skeletal disorders: too much of a good thing", *TIG*, vol. 13, No. 5, May 1997, pp. 178–182.

Womack et al., "Bovine genome mapping: evolutionary inference and the power of comparative genomics", *Current Opinion in Genetics & Development*, 1995, 5:725–733.

* cited by examiner

```
HUMAN   ETGGTCCTTGGGGTCCTGCTCCTGGGAGATCTTCACGCTGGGGGGCTCCCCGTACCCCGGCATCCCTGTG
MURINE  T.....T...T......C..........T.............A....T.T..........A...
OVINE   G...........C........................G.......T.............C.*.

HUMAN   TrpSerPheGlyValLeuLeuTrpGluIleIlePheThrLeuGlyGlySerProTyrProGlyIleProVal
MURINE  ...........................................................
OVINE   ...........................................................***

HUMAN   GAGGAGCTCTTCAAGCTGCTGAAGGAGGGCCACCGCATGGACAAGCCCGCCAACTGCACACACGACCT
MURINE  ..A......T.......T..A..........A..G.............T......
OVINE   .................A.............G.............G..T....

HUMAN   GluGluLeuPheLysLeuLeuLysGluGlyHisArgMetAspLysProAlaAsnCysThrHisAspLeu
MURINE  ...........................................................
OVINE   ................................................Ser..........

FIG. 3
```

|  |  | kinase I |  |  | kinase II |  |
|---|---|---|---|---|---|---|
| HUMAN | 551 | LYVLVEYAAKGNLREFLRARRPPG | LDYSFDTCKPPEEQLTFKDLVSCAYQ |
| MOUSE | 545 | LYVLVEYAAKGNLREFLRARRPPG | LDYSFDTCKPPEEQLTCKDLVSCAYQ |
| NORMAL | 424 | LYVLVEYAAKGNLREYLRARRPPGM | DYSFDACRLPEEQLTCRLPEEQLTFKDLVSCAYQ |
| SPIDER | 551 | LYVLVEYAAKGNLREYLRARRPPGT | DYSFDTCRLPEEQLTFKDLVSCAYQ |

| HUMAN | 601 | VARGMEYLASQKCIHRDLAARNVLVTEDNVMKIADFGLARDVHNLDYYKK |
| MOUSE | 595 | VARGMEYLASQKCIHRDLAARNVLVTEDNVMKIADFGLARDVHNLDYYKK |
| NORMAL | 474 | VARGMEYLASQKCIHRDLAARNVLVTEDNVMKIADFGLARDVHNLDYYKK |
| SPIDER | 601 | VARGMEYLASQKCIHRDLAARNVLVTEDNVMKIADFGLARDVHNLDYYKK |

| HUMAN | 651 | TTNGRLPVKWMAPEALFDRVYTHQSDVWSFGVLLWEIFTLGGSPYPGIPV |
| MOUSE | 645 | TTNGRLPVKWMAPEALFDRVYTHQSDVWSFGVLLWEIFTLGGSPYPGTPV |
| NORMAL | 524 | TTNGRLPVKWMAPEALFDRVYTHQSDVWSFGVLLWEIFTLGGSPYPGIPV |
| SPIDER | 651 | TTNGRLPVKWMAPEALFDRVYTHQSDVWSFGVLLWEIFTLGGSPYPGIPE | kinase II

| HUMAN | 701 | EELFKLLKEGHRMDKPANCTHDLYMTMRECWHAAPSQRPTFKQLVEDLDR |
| MOUSE | 695 | EELFKLLKEGHRMDKPASCTHDLYMTMRECWHAAPSQRPTFKQLVEDLDR |
| NORMAL | 574 | EELFKLLKEGHRMDKPANCTHDLYMTMRECWHAVPSQRPTFKQLVEDLDR |
| SPIDER | 701 | EELFKLLKEGHRMDKPANCTHDLYMTMRECWHAAPSQRPTFKQLVEDLDR |

| HUMAN | 751 | VLTVTSTDEYLDLSAPFEQYSPGGQDTPSSSSSGDDSVFAHDLLPPAPPS |
| MOUSE | 745 | ILTVTSTDEYLDLSVPFEQYSPGGQDTPSSSSSGDDSVFTHDLLPGPPS |
| NORMAL | 624 | VLTVTSTDEYLDLSVPFEQYSPGGQDTPSSGSSGDDSVFAHDLLPAP-G |
| SPIDER | 751 | VLTVTSTDEYLDLSVPFEQYSPGGQDTPSSGSSGDDSVFAHDLLPAP-G |

*FIG. 6*

SCREENING FOR THE MOLECULAR DEFECT CAUSING SPIDER LAMB SYNDROME IN SHEEP

This application claims priority from United States Ser. No. 60/050,127 filed on Jun. 18, 1997.

GOVERNMENT RIGHTS

The research underlying this invention was partially funded by the USDA/NRI competitive grants' program USDA/NRICGP #92-02511, #96-35205, and #97-03988. The U.S. government may have some rights in this invention.

TECHNICAL FIELD

The present invention relates to the field of genetics. Specifically, the present invention relates to materials and methods used to isolate and detect a genetic defect in the fibroblast growth factor receptor 3 gene such as the defect that causes "Spider Lamb Syndrome" in sheep.

BACKGROUND

"Spider Lamb Syndrome" or "hereditary chondrodysplasia" is a semi-lethal congenital disorder in sheep causing severe skeletal abnormalities. These abnormalities can include abnormally long, spider-like legs, humped and twisted spines, deformed ribs and sternebra, facial deformities, lack of body fat, and underdevelopment of muscle. The most severe lesions progress to compression fractures from mechanical stress due to abnormal limb angulation. Vanek et al. "Comparing spider syndrome in Hampshire and Suffolk sheep", Vet. Med., 82:430–437 (1987). Radiological evaluation of Spider lamb shoulders, elbows and sternum reveal multiple, irregular islands of ossification. Vanek et al. "Radiographic diagnosis of hereditary chondrodysplasia in newborn lambs", JAVMA, 194:244–248 (1989). Histologic examinations of the vertebrae and long bones indicate an increase in width of the zone of proliferation, as well as hypertrophy and unevenness of the growth cartilage. Chondrocytes appear vacuolated and disorganized, lining up in bent nonparallel columns. Rook et al. "Diagnosis of hereditary chondrodysplasia (spider lamb syndrome) in sheep", JAVMA, 188:713–718 (1988), Troyer et al. "A morphologic and biochemical evaluation of the spider syndrome in Suffolk sheep", Anat. Histol. Embryol., 17:289–300 (1988). However, there are no deformities in the chondrocyte organelles (Troyer et al., 1988), suggesting that no problem exists with structural components of the cells themselves. Also, no chromosomal abnormalities can be found in Spider lambs. Vanek et al. "Comparison of G-banded chromosomes from clinically normal lambs and lambs affected with ovine hereditary chondrodysplasia (spider syndrome)", Am J. Vet. Res., 49:1164–1168 (1988).

Spider lamb Syndrome was first identified in newborn black-faced lambs during the mid-1970's. The syndrome has since surfaced in several sheep breeds in the United States and Canada within the last two decades. Such sheep breeds, include, but are not limited to, North American Suffolks and Hampshires, and United States Southdowns, Oxfords and Shropshires. In addition, cases of Spider Lab Syndrome have been reported in New Zealand and Australia, after the importation of several United States Suffolk rams into Australia in the early 1990's. It is believed this disorder arose as a mutation in a Suffolk genetic line that was used heavily during the late 1960's because of desirable production and show-ring characteristics.

Breeding studies have established that the gene responsible for this disease has an autosomal recessive mode of inheritance. Thomas and Cobb, "Spider syndrome and other genetic defects'", Sheep Mag. 7:44–46 (1986); Berg et al. "The mode of inheritance of the 'Spider' Lamb Syndrome in Suffolk sheep", SID Res. Digest 4:1–3 (1987); Vanek et al., (1989). Thus, animals with two copies of the normal form (allele) of the gene are normal in appearance (homozygous normal or "NN") as are, most often, animals with one copy of the normal allele and one copy of the Spider Lamb Syndrome ("SLS") allele (heterozygous normal or "NS") . However, the homozygous normal animal can never produce a Spider offspring whereas the heterozygous or carrier animal has about 25% Spider offspring if mated to another carrier. Those animals with two copies of the SLS allele have the Spider phenotype and are rarely used for breeding purposes. While dramatic culling of all suspected carriers would reduce the frequency of the gene, it is a long and very expensive process. Progeny testing of potential breeding rams is another method of reducing gene frequency but it is also costly.

Due to SLS's recessive nature, it would be a significant improvement in the art to have a diagnostic or genetic screening test to determine, for example, whether or not a sheep is a carrier of the gene for SLS.

DISCLOSURE OF THE INVENTION

The invention includes genetic markers for diagnosing whether a sheep carries the gene for SLS. The genetic markers are based upon the discovery of polymorphisms in the sheep ("ovine") fibroblast growth factor receptor 3 ("FGFR3") gene, which can be used in genetic typing of sheep for this defect. Thus, the markers can be used as selection tools for eliminating SLS carrier animals from a sheep flock. The invention also includes the isolated defective gene for SLS itself.

The invention also includes methods for screening sheep to differentiate those that possess no ("NN"), one ("NS") , or two ("SS") copies of the Spider Lamb Syndrome defect. In addition, methods are described for identifying other markers associated with Spider Lamb Syndrome. The markers are based upon the presence or absence of certain polymorphisms in the ovine fibroblast growth factor receptor 3 gene. Preferably, the polymorphisms are detected as polymerase chain reaction-restriction fragment length polymorphisms ("PCR-RFLP") and/or single strand conformational polymorphisms ("SSCP").

One aspect of the invention involves a method to screen a mammal, such as a sheep, to determine the mammal's genetics with respect to FGFR3, such as that causing Spider Lamb Syndrome in sheep. A biological sample containing genomic DNA is first obtained from the mammal. A biological sample is a sample of tissue or fluid suspected of containing an analyte polynucleotide or mutant or normal FGFR3 including, but not limited to, for example, plasma, serum, spinal fluid, lymph fluid, external sections of skin, respiratory, intestinal, and genitourinary tracts, tears, saliva, brain, cartilage, bone, blood cells, organs, tissue from a subject mammal and samples of in vitro cell culture constituents. The particular biological sample is then analyzed to determine whether or not a polymorphism exists in the fibroblast growth factor receptor 3 gene or the receptor itself. The presence or absence of a specific fragment or RFLP pattern or the detection of the herein described nucleotide difference may be determined by, but not limited to, polymerase chain reaction-restriction fragment length polymorphisms, direct sequencing, or single strand conformational polymorphisms.

The invention also includes a protein which includes a polypeptide comprising a mutant FGFR3, wherein the modification associated with mutation involves substituting an amino acid other than valine at, for example, position 23 of SEQ ID NO:9. Such substitution will generally be a substitution with a polar amino acid such as arginine, aspartic acid, asparagine, cysteine, glutamic acid, glutamine, glycine, histidine, lysine, serine, threonine, and tyrosine, especially glutamic acid.

The present invention also provides isolated antibodies, preferably monoclonal antibodies, which specifically bind to an isolated polypeptide comprised of at least amino acid residues of the mutant FGFR3.

The invention also includes kits useful for the diagnosis of mutant or wild-type FGFR3. Such kits include a kit suitable for use in the screening technique and for assaying for the presence of the FGFR3 gene by an immunoassay which comprises an antibody which specifically binds to a gene product of the FGFR3 gene, and reagent means for detecting the binding of the antibody to the gene product, the antibody and reagent means each being present in amounts effective to perform the immunoassay.

A kit according to the invention for assaying for the presence for the FGFR3 gene in a mammal by hybridization assay techniques includes oligonucleotide sequences for PCR priming of the appropriate mammalian genomic sequence; oligonucleotide probes which specifically bind to the FGFR3 gene; and reagent means for detecting the hybridization of the oligonucleotide probes to the FGFR3 gene; the probes and reagent means each being present in amounts effective to perform the hybridization assay.

BRIEF DESCRIPTION OF THE FIGURES

FIG. 3 depicts the alignment of nucleotide and amino acid sequences for exon 17 of the human, mouse, and ovine FGFR3 genes, both normal (SEQ ID NO:9) and Spider (wherein Xaa of SEQ ID NO:2 is glutamic acid) alleles. Conserved nucleotides are represented by dots (.) and amino acids by hyphens (-). The * represents the herein identified T→A nucleotide substitution, and *** represents the valine to glutamic acid amino acid substitution between normal and Spider alleles, respectively.

FIG. 6 depicts the amino acid of valine/glutamic acid at amino acid position 700 found within the second tyrosine kinase domain of exon 17, the SLS FGFR3 mRNA.

DETAILED DESCRIPTION AND BEST MODE OF THE INVENTION

A. General

Figure 1:
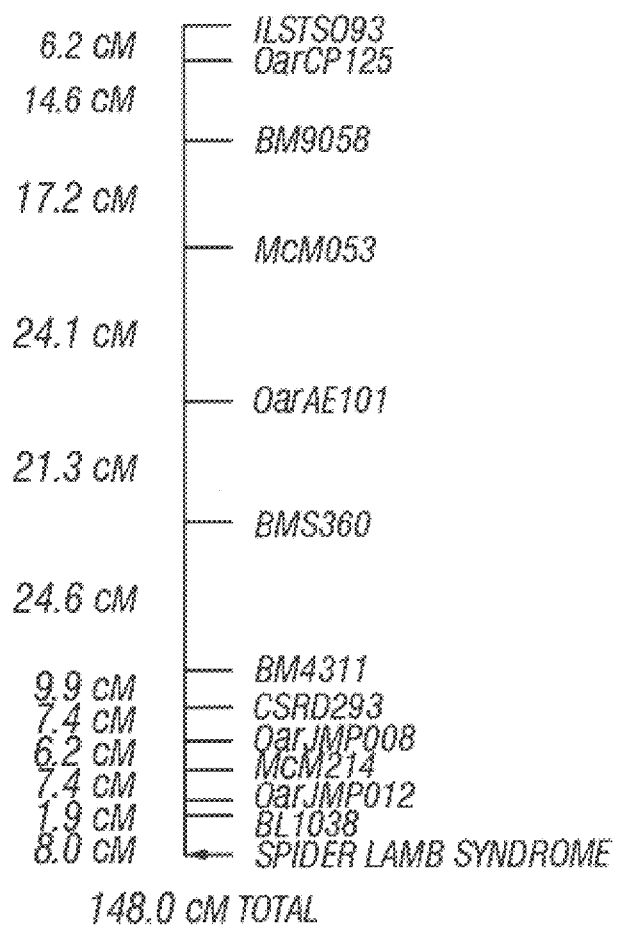
FIG. 1 depicts the linkage map of ovine chromosome 6. Map positions are given in centiMorgans ("cM") starting from the proterminal marker. All distances were sex-averaged and recombination units were converted to cM using Kosambi's mapping function.

As described herein, the invention preferably relates to methods and materials used to isolate and detect a recessive gene causative for SLS. In the case of a sheep suffering from SLS, these methods can include detecting the mutant FGFR3 itself, for example by the use of labeled antibodies directed specifically against the mutant receptor.

More specifically however, the invention relates to germline mutations in the FGFR3 gene which cause disease, particularly Spider Lamb Syndrome in sheep. The invention has implications in the area of gene therapy for Spider Limb Syndrome and related disorders. The invention also relates to the screening of the FGFR3 gene for mutations, which screening is useful for, among other things, determining whether a mammal, such as a sheep, carries a gene coding for the mutant FGFR3 protein as identified herein.

The present invention specifically provides an isolated polynucleotide comprising all, or a portion of the mutant FGFR3 gene, preferably at least eight bases and not more than about fifteen kilobases in length. Such polynucleotides may be antisense polynucleotides. As more thoroughly described herein, the present invention also provides a recombinant construct comprising such an isolated polynucleotide, for example, a recombinant construct suitable for expression in a transformed host cell.

The ovine FGFR3 gene sequenced in SEQ ID NO:10 extends from the 3' end of exon 3 through the end of exon 19, including the translation stop codon. The W indicates the A- or T-mutation that causes SLS. There is also a polymorphism (G or C only present in normal alleles) that makes no change in the amino acid sequence (Ser 455 Ser) which is not noted in the sequence.

As used herein, "isolated" or "substantially pure" nucleotide (e.g., RNA, DNA or a mixed polymer) or peptide is one which is substantially separated from other cellular components which naturally accompany a native human sequence or protein, for example, ribosomes, polymerases, other genome sequences and proteins. The term embraces a nucleic acid sequence or peptide which has been removed from its naturally occurring environment, and includes, but is not limited to, recombinant or cloned DNA isolates and chemically synthesized analogs, or analogs biologically synthesized by heterologous systems.

In the case of proteins or polypeptides, "isolated", "substantially pure", and "substantially homologous" are used to describe a protein or polypeptide (e,g., a FGFR3 polypeptide) which has been separated from components which accompany it in its natural state. A monomeric protein is substanially pure when at least about 60 to 75% of a sample exhibits a single polypeptide sequence. A substantially pure protein will typically comprise about 60 to 90% (weight/weight) of a protein sample, more usually about 95%, and preferably will over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by HPLC or other means utilized in the art for purification. Furthermore, a polypeptide expressed as an expression product of an isolated and manipulated genetic sequence is an "isolated polypeptide", as used herein, even if expressed in a homologous cell type. Synthetically made forms or molecules expressed by heterologous cells are inherently isolated molecules.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e,g., methyl phosphonates, phosphotriesters, phosphoamidates, carbamates, etc.), charged linkages (e.g., phosphorothioates, phosphorodithioates, etc.), pendant moieties (e.g., polypeptides), intercalators (e.g., acridine, psoralen, etc.), chelators, alkylators, and modified linkages (e.g., alpha anomeric acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

With the disclosure herein, one of skill in the art would have the ability to prepare recombinant nucleic acids comprising all or part of the nucleotide encoding the mutant FGFR3 protein causative of SLS. A recombinant nucleic acid is a nucleic acid which is not naturally occurring, or which is made by the artificial combination of two otherwise separated segments of a sequence. This artificial combination may be accomplished by either chemical synthesis or by the artificial manipulation of isolated segments of nucelic acids, for example, by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

As used herein, "FGFR3 protein" or "FGFR3 polypeptide" refer to a protein or polypeptide encoded by the FGFR3 locus, variants or fragments thereof. The term "polypeptide" refers to a polymer of amino acids and its equivalent and does not refer to a specific length of the product. Thus, peptides, oligopeptides, and proteins are included within the definition of a polypeptide. The term "polypeptide" does not exclude polypeptide modifications, such as, for example, glycosylation, acetylation, phosphorylation, and the like. Included within the definition are, for example, polypeptides containing one or more analogs of an amino acid (including, for example, unnatural amino acids), polypeptides with substituted linkages as well as other modifications known in the art, both naturally and not naturally occurring. Ordinarily, such polypeptides will be at least 50% homologous to the native FGFR3 sequence, preferably in excess of 90%, and more preferably at least about 95 % homologous. Also included are proteins encoded by DNA which hybridize under high or low stringency conditions, to FGFR3-encoding nucleic acids and closely related polypeptides or proteins retrieved by, for example, antisera to the FGFR3 protein(s).

The recombinant construct may be capable of replicating autonomously in a host cell. The recombinant construct may also become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of the polynucleotide with which it is associated in nature; 2) is linked to a polynucleotide other than that to which it is linked in nature; or 3) does not occur in nature. Therefore, recombinant nucleic acids comprising sequences otherwise not naturally occurring are provided by this invention. Although the wild-type sequence (e.g., one encoding a protein including the polypeptide of SEQ ID NO:9) may be employed, it will often be altered, for example, by deletion, substitution or insertion.

Typically, a promoter is operably linked to a coding sequence so that the promoter affects the coding sequence's transcription or expression. "Operably linked" means that the components are in a relationship permitting them to function in their intended matter.

cDNA or genomic libraries of various types may be screened as natural sources of the nucleic acids of the present invention, or such nucleic acids may be provided by amplification of sequences resident in genomic DNA, other natural sources, or libraries (e.g., BAC library), for example, by PCR. The choice of cDNA libraries normally corresponds to a tissue source which is abundant in mRNA for the desired protein. Clones of a library are spread onto plates, transferred to a substrate for screening, denatured and probed for the presence of the desired sequences.

Techniques for nucleic acid manipulation are described generally, for example, in Sambrook et al. *Molecular Cloning: A laboratory Manual* (2d ed., Cold Spring Harbor Laboratory, Cold Spring Harbor, N.Y., US 1989) or Ausubel et al. *Current Protocols in Molecular Biology* (J. Wiley and Sons, NY, US, 1992). Reagents useful in applying such techniques, such as restriction enzymes and the like, are widely known in the art and commercially available from such vendors as New England BioLabs, Amersham, Promega Biotec, U.S. Biochemicals, New England Nuclear, and a number of other sources. The recombinant nucleic acid sequences may be used to produce fusion proteins of the instant invention may be derived from natural or synthetic sequences. Many natural gene sequences are available from various cDNA or from genomic libraries using appropriate probes. See, GenBank.

Also provided by the present invention are methods of detecting a polynucleotide comprising a portion of locus or its expression product in an analyte. Such methods may further comprise the step of amplifying the portion of the FGFR3 locus. The method is useful for the diagnosis of SLS or the determination of whether or not an animal carries a gene coding for the mutant FGFR3.

Amplification of polynucleotides generally utilizes methods such as the polymerase chain reaction, ligase amplification (or ligase chain reaction, LCR) and amplification methods based on the use of Q-beta replicase. These methods are well known, and widely practiced in the art. See, e.g., U.S. Pat. Nos. 4,683,195 and 4,683,222 and Innis et al. *PCR Protocols: A guide to Methods and Applications,* (Academic Press, San Diego, Calif., 1990) for PCR, and Wu et al. *Genomics,* 4:560–5699 (1989) for LCR. Reagents and hardware for conducting PCR are commercially available. Primers to amplify sequences from the FGFR3 region are preferably complementary to, and hybridize specifically to sequences in the FGFR3 region or in regions that flank a target region therein. FGFR3 sequences generated by amplification may be sequenced directly. Alternatively, an amplified sequence may be cloned prior to sequence analysis. A method for direct cloning and sequence analysis is described in Scharf, *Science,* 233:1076 (1986).

As used herein, FGFR3 region refers to the portion of ovine chromosome 6 (or other mammalian genomic sequence containing the FGFR3 region such as human chromosome 4 or murine chromosome 5) that contains the FGFR3 locus, including the FGFR3 gene. FGFR3 locus, PGFR3 allele, and FGFR3 region refer to the double-stranded DNA comprising the locus, allele or region, as well as either of the single-stranded DNAs comprising the locus, allele or region.

B. Polynucleotide and Peptide Preparation

The invention also provides methods for preparing a polynucleotide comprising polymerizing nucleotides to yield a sequence comprised of at least eight consecutive nucleotides of the SLS or mutant FGFR3 locus; and methods of preparing a polypeptide or oligopeptide comprising polymerizing amino acids to yield a sequence comprising at least five amino acids encoded within the SLS or mutant FGFR3 locus.

A polynucleotide is said to "encode" a polypeptide if, in its native state or when manipulated by methods well known to those skilled in the art, it can be transcribed and/or translated to produce the mRNA for and/or the polypeptide or a fragment thereof. The antisense strand is the complement of such a nucleic acid, and the encoding sequence can be deduced therefrom.

Polypeptides and oligopetides according to the general formula may be prepared in a manner conventional for such compounds. To that end, suitably $N^\alpha$ protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc"). group. The Z group can also be removed by catalytic hydrogenation. Other suitable protecting groups include the Nps, Bmv, Bpoc, Aloc, MSC, etc. A good overview of amino protecting groups is given in *The Peptides, Analysis, Synthesis, Biology*, Vol. 3 E. Gross and J. Meienhofer, eds., (Academic Press, New York, 1981). Protection of carboxyl groups can take place by ester formation i, base-labile esters like methyl or ethyl, acid labile esters like tert. butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in *The Peptides, Analysis, Synthesis, Biology* id. or in *Pure and Applied Chemistry*, 59(3), 331–344 (1987). Activation of the carboxyl group of the suitably protected amino acids or peptides can take place by the azide, mixed anhydride, active ester, or carbodiimide method especially with the addition of catalytic and racemization-suppressing compounds like 1-N-N-hydroxybenzotriazole, N-hydroxysuccinimide, 3-hydroxy-4-oxo-3,4-dihydro-1,2,3,-benzotriazine, N-hydroxy-5-norbornene-2,3-dicarboxyimide. Also the anhydrides of phosphorus based acids can be used. See, e.g. *The Peptides, Analysis, Synthesis, Biology*, supra and *Pure and Applied Chemistry*, 59(3), 331–344 (1987).

It is also possible to prepare the compounds by the solid phase method of Merrifield. Different solid supports and different strategies are known see, e.g. Barany and Merrifield in *The Peptides, Analysis, Synthesis, Biology*, Vol. 2, E. Gross and J. Meienhofer, eds., (Acad. Press, N.Y., 1980), Kneib-Cordonier and Mullen *Int. J. Peptide Protein Res.*, 30, 705–739 (1987) and Fields and Noble *Int. J. Peptide Protein Res.*, 35 161–214 (1990). The synthesis of compounds in which a peptide bond is replaced by an isostere, can, in general, be performed using the previously described protecting groups and activation procedures. Procedures to synthesize the modified isosteres are described in the literature, for, for example, the —$CH_2$—NH— isostere and for the —CO—$CH_2$— isostere.

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g., Volumes 3, 5 and 9 of the series on *The Petides Analysis, Synthesis, Biology*, supra.

Another possibility is the application of enzymes in synthesis of such compounds; for reviews see, e.g., H. D. Jakubke in *The Peptides, Analysis, Synthesis, Biology*, Vol. 9, S. Udenfriend and J. Meienhofer, eds., (Acad. Press, N.Y., 1987).

Oligopeptides or polypeptides according to the invention may also be made according to recombinant DNA methods. Such methods involve the preparation of the desired oligopeptide thereof by means of expressing recombinant polynucleotide sequence (e.g., that of SEQ ID NO:1) which codes for the oligopeptides or polypeptide in question in a suitable microorganism as host. Generally the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eucaryotic or procaryotic host cell, and culturing the host cell thus transformed. When a eucaryotic host cell is used, the compound may include a glycoprotein portion.

Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage & Carruthers, *Teta. Letters*, 22:1859–1862 (1981) or the triester method according to Matteucci and Caruthers, *J. Am. Chem. Soc.*, 103:3185 (1981), and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prpared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence ("ARS") and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native FGFR3 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with FGFR3 genes. Examples of workable combinations of cell lines and expression vectors are described in Sambrook et al., 1989 or Ausubel et al., 1992; see also, e.g., Metzger et al. *Nature,* 334:31–36 (1988). Many useful vectors are known in the art and may be obtained from such vendors as Stratagene, New England Biolabs, Promega Biotech, and others. Promoters such as the tip, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al. *Nature,* 273:113 (1978)) or promoters derived from murine Moloney leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression,* (Cold Spring Harbor Press, Cold Spring Harbor, N.Y., US 1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g., ampicllin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resuing RNA introduced into the host cell by well-known methods, e.g., by injection (see, Kubo et al. *FEBS Letts,* 241:119 (1988)), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retoviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the FGFR3 nucleic acids or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, *Cell Culture. Methods in Enzymology,* vol. 58 (Academic Press, San Diego, Calif., US 1979). Examples of commonly used mammalian host cell lines are VERO and HeLa cells, Chinese hamster ovary (CHO) cells, and WI38, BHK, and COS cell lines, although it will be appated by the sldlled practitioner that other cell lines may be apprreriate, for example, to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transfornant may be selected, for example, by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of FGFR3 polypeptides.

Antisense polynucleotide sequences are useful in preventing or diminishing the expression of the FGFR3 locus, as will be appreciated by those skilled in the art. For example, polynucleotide vectors containing all or a portion of the FGFR3 locus or other sequences from the FGFR3 region (particularly those flanking the FGFR3 locus) may be placed under the control of a promoter in an antisense orientation and introduced into a cell. Expression of such an antisense construct within a cell will interfere with FGFR3 transcription and/or translation and/or replication.

The probes and primers based on the FGFR3 gene sequences disclosed herein are used to identify homologous FGFR3 gene sequences and proteins in other species. These FGFR3 gene sequecees and proteins are used in the diagnostic/prognostic, therapeutic and drug screening mehods described herein for the species from which they have been isolated.

Protein modifications or fiagments are provided by the instant invention for FGFR3 polypeptides or fragments thereof which are substantially homologous to the primary structural sequence, but which include, for example, in vivo or in vitro chemical and biochemical modifications or which incorporate unusual amino acids. Such modifications include, for example, acetylation, carboxylation, phosphorylation, glycosylation, ubiquitination, labeling, as otherwise described herein, and other modifications apparent to those of skill in the art.

Besides substantially full length polypeptides, the present invention provides for biologically active (e.g., immunologically active) fragments of the polypeptides. For immunological purposes (e.g., useful in the production of antibodies against the SLS FGFR3 protein), tandem repeat polypeptide sequences contaning the valine to glutamic acid substitution of the mutant FGFR3 (SEQ ID NO:1) may be used to as immunogens thereby producing highly antigenic proteins.

A "fragment", "portion", or "segment" of a polypeptide or protein is a stretch of amino acid residues of at least about five to seven contiguous amino acids, often at least about seven to nine contiguous amino acids, typically at least about nine to thirteen contiguous amino acids, and, most preferably, at least about twenty to thirty or more contiguous amino acids.

The present invention also provides for fusion proteins, comprising FGFR3 polypeptides and fragments. Homologous polypeptides may be fusions between two or more FGFR3 polypeptide sequences or between the sequences of FGFR3 and a related protein. Likewise, heterologous fusions may be constructed which would exhibit a combination of properties or activities of the derivative proteins. Such fusion proteins will typically be made by recombinant nucleic acid methods.

C. Methods for Screening Animals

The invention also provides methods of screening the FGFR3 gene to identify mutations. Such methods may include the step of amplifying a portion of the SLS or FGFR3 locus, and may futrer include the step of providing polynucleotides that are primers for amplification of the portion of the SLS or FGFR3 locus or detection involving the hybridization of a probe or primer, direct sequencing, etc.

The detection of specific DNA sequence may be achieved by methods such as hybridization using specific oligonucleotides (Wallace et al. *Cold Spring Harbor Symp. Quant. Biol.,* 51:257–261 (1986)), direct DNA sequencing (Church and Gilbert, *Proc. Nat. Acad. Sci. USA,* 81:1991–1995 (1988)), the use of restriction enzymes (Flavell et al. *Cell* 15:25 (1978), Geever et al *Proc. Nat. Acad. Sci. USA,* 78:5081 (1981)), discrimination on the basis of electrophoretic mobility in gels with denaturing reagent (Myers and Maniatis, *Cold Spring Harbor Sym. Quant. Biol.,* 51:275–284 (1986)), temperature gradient gel electrophoresis, RNase protection (Myers et al. *Science* 230:1242 (1985)), chemical cleavage (Cotton et al. *Proc. Nat. Acad. Sci. USA,* 85:4397–4401 (1985)) and the ligase-mediated detection procedure (Landegren et al *Science* 241:1077 (1988)).

Oligonucleotides specific to normal or mutant sequences are chemically synthesized using commercially available machines, labelled radioactively with isotopes (such as .sup.32 P) or non-radioactively (with tags such as biotin (Ward and Langer et al. *Proc. Nat. Acad. Sci. USA,* 78:6633–6657 (1981), and hybridized to individual DNA samples immobilized on membranes or other solid siports by dot-blot or transfer from gels after electrophoresis. The presence or absence of these specific sequences are visualized by methods such as autoradiography or fluorometric (Landegren et al, 1989, supra) or colorimetric reactions (Gebeyehu et al. *Nucleic Acids Research,* 15:4513–4534 (1987)). As is appreciated by those skilled in the art, the sequence length of the oligonucleotides is sufficient to ensure hybridization of the probe. Usually the oligos of subject material are approximately 12 to 20 base pairs and up; for example, the specific probes of SEQ ID NO:4 and SEQ ID NO:6 form the preferred embodiment of the invention.

Sequence differences between normal and mutants may be revealed by the direct DNA sequencing method of Church and Gilbert, supra. Cloned DNA segments may be used as probes to detect specific DNA segments. The sensitivity of this method is greatly enhanced when combined with PCR (Wrichnik et al. *Nucleic Acids Res.,* 15:529–542 (1987); Wong et al. *Nature,* 330:384–386 (1987); Stoflet et al. *Science,* 239:491–494 (1988)). In the latter procedure, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent-tags.

Sequence alterations may occasionally generate fortuitous restriction enzyme recognition sites which are revealed by the use of appropriate enzyme digestion followed by conventional gel-blot hybridization. Southern, *J. Mol. Biol.,* 98: 503 (1975). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

It is possible to modify the sequence of the DNA in order to incorporate a restriction enzyme recognition site suitable for detection of a single nucleotide difference.

Genetic testing based on DNA sequence differences may be achieved by detection of alteration in electrophoretic mobility of DNA fragments in gels with or without denaturing reagent. Small sequence deletions and insertions can be visualized by high resolution gel electrophoresis. For example, the PCR product with the 1 bp substitution is clearly distinguishable from the normal sequence on an 8% non-denaturing polyacrylamide gel. DNA fiagments of different sequence compositions may be distinguished on denaturing formamide gradient gel in which the mobilities of different DNA fragments are retarded in the gel at different positions according to their specific "partial-melting" temperatures. Myers, supra. In addition, sequence alterations, may be detected as changes in the migration pattern of DNA heteroduplexes in non-denaturing gel electrophoresis, as have been detected for the 1 bp mutation and in other experimental systems. Nagamine et al. *Am. J. Hum. Genet,* 45:337–339 (1989). Alternatively, a method of detecting a mutation comprising a single base substitution or other small change could be based on differential primer length in a PCR. For example, one invariant primer could be used in addition to a primer specific for a mutation. The PCR products of the normal and mutant genes can then be differentially detected in acrylamide gels.

Sequence changes at specific locations may also be revealed by nuclease protection assays, such as RNase (Myers, supra) and S1 protection (Berk & Sharpe, *Proc. Nat. Acad. Sci. USA,* 75:1274 (1978)), the chemical cleavage method (Cotton, supra) or the ligase-mediated detection procedure (Landegren supra).

In addition to conventional gel-electrophoresis and blot-hybridization methods, DNA fragments may also be visualized by methods where the individual DNA samples are not immobilized on membranes. The probe and target sequences may be both in solution or the probe sequence may be immobilized. Saiki et al. *Proc. Natl. Acad. USA*, 86:6230–34 (1989). A variety of detection methods, such as autoradiography involving radioisotopes, direct detection of radioactive decay (in the presence or absence of scintillant), spectrophotometry involving colorigenic reactions and fluorometry involving fluorogenic reactions, may be used to identify specific individual genotypes.

In summary, the screening method comprises the steps of: providing a biological sample of the subject to be screened; and providing an assay for detecting in the biological sample, the presence of at least a member from the group consisting of the normal ovine FGFR3, normal FGFR3 products, an SLS mutant FGFR3, SLS mutant FGFR3 products and mixtures thereof.

The method may be further characterized by including at least one more nucleotide probe which is a different DNA sequence fragment of, for example, the DNA of SEQ ID NO:1, or a different DNA sequence fragment of ovine chromosome 6 and located to either side of the DNA sequence of SEQ ID NO:1.

Polynucleotide polymorphisms associated with FGFR3 alleles which, for example, predispose a sheep to SLS are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. Since such indications identify neutral DNA polymorphisms, as well as mutations, these indications may need further analysis to demonstrate detection of a Spider allele.

Probes for FGFR3 alleles may be derived from the sequences of the FGFR3 region or its cDNAs. The probes may be of any suitable length, which span all or a portion of the FGFR3 region, and which allow specific hybridization to the FGFR3 region. If the target sequence contains a sequence identical to that of the probe, the probes may be short, for example, in the range of about 8 to about 30 base pairs, since the hybrid will be relatively stable under even stringent conditions. If some degree of mismatch is expected with the probe, i.e., it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labelling probes see, for example, Sambrook et al. 1989 or Ausubel et al. 1992. Other similar polynucleotides may be selected by using homologous polynucleotides. Alternatively, polynucleotides encoding the FGFR3 polypeptides or similar polypeptides may be synthesized or selected by use of the redundancy in the genetic code. Various codon substitutions may be introduced, for example, by silent changes (thereby producing various restriction sites) or to optimize expression for a particular system. Mutations may be introduced to modify the properties of the polypeptide.

Probes comprising synthetic oligonucleotides or other polynucleotides of the present invention may be derived from naturally occurring or recombinant single-stranded or double-stranded polynucleotides, or be chemically synthesized. Probes may also be labeled by nick translation, Klenow fill-in reaction, or other methods known in the art.

Primer pairs according to the instant invention are useful for determining the nucleotide sequence of a particular FGFR3 allele using, for example, PCR. The pairs of single stranded DNA primers can be annealed to sequences within or surrounding the FGFR3 gene on the chromosome of the particular mammal being analyzed with the primers (e.g., ovine chromosome 6) in order to prime amplifying DNA synthesis of the FGFR3 gene itself. A complete set of these primers allows synthesis of all of the nucleotides of the FGFR3 gene coding sequences. Allele-specific primers can also be used. Such primers anneal only to particular FGFR3 mutant or the normal alleles, and thus will only amplify a product in the presence of the mutant or normal allele as a template, repectively.

In order to facilitate subsequent cloning of amplified sequences, primers may have restriction enzyme sites appended to their 5' ends. Thus all nucleotides of the primers are derived fiom FGFR3 sequences or sequences adjacent to FGFR3, except for the nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the information of SEQ ID NO:1, design of particular primers is well within the skill of the art.

The nucleic acid sequences provided by the instant invention are useful for a number of purposes. These sequences can be used to develop probes for Southern hybridization of genomic DNA and in the RNAse protection method for detecting point mutations as disclosed herein. The sequences can be used to develop primers for PCR amplification products. The sequences may also be used to detect mismatches with the FGFR3 gene or mRNA using other techniques.

In a method to screen a sheep to determine its genetics with respect to Spider Lamb Syndrome, a sample of genomic DNA is first obtained from the sheep, such as from the sheep's blood or other tissue sample. The genomic DNA sample is then analyzed to determine whether or not a polymorphism exists in the fibroblast growth factor receptor 3 gene. The presence or absence of a specific fragment, difference in nucleotide sequence, or RPLP pattern may be determined by, for example, polymerase chain reaction-restriction fragment length polymorphisms or single strand conformational polymorphisms. This determination preferably involves the following steps:

SSCP ananlysis. Reactions to detect SSCP conain ovine genomic DNA, primers that flank the region of interest, dNTPs, KCl, TRIS™, the appropriate $MgCl_2$ concentration, $[a^{32}P]dCTP$, and Taql DNA polymerase. Samples are processed through 1 cycle of 4 min at 940° C., followed by 30–34 cycles of 1 min at 94° C., 1 minute at the appropriate annealing temperature and 1 min at 72° C., and ending with 5 min at 72° C. and 5 mm at 4° C. If necessary, amplified DNA is digested with the appropriate restriction enzyme at the appropriate tempemtin. The final DNA solution is mixed with 2 vol of formamide sample buffer (95% formamide, 10 mM EDTA pH 8.0, 1 mg/mL xylene cyanol FF, 1 mg/mL bromophenol blue) containing 20 mM NaOH, denatured for 10 min at 100° C., and then chilled on ice. PCR products are separated on 0.5×MDE gels (FMC BioProducts, Rockland, Me., US). Gels are exposed to Kodak XAR-5™ diagnostic film at −70° C.

PCR-RFLP ansis. When running PCR-RFLP maikers, the [$a^{32}P$]dCTP is omitted from the PCR reaction. Following enzyme digestion, reactions are mixed with loading buffer and analyzed by standard polyacrylamide gel electrophoresis ("PAGE"). Gels may be stained in ethidium bromide and the DNA fragments visualized under ultra violet light. Other methods known to those of skill in the art may be used.

In performing the SLS genetic marker test, a single blood sample can be taken from a newborn lamb or an older sheep and evaluated for its SLS genotype (normal, carrier or diseased). Those animals that are carrers of the defect can be eliminated from the breeding herd without further testing. In addition, an ovine embryo can be tested for the defect by obtaining genomic DNA from a few of the embryo's cells. Those embryos that are homozygous normal would be suitable for embryo transfer.

D. Antibodies

Antibodies against the mutant receptor protein of SEQ ID NO: 2 for use in diagnostic kits and methods according to the invention are preferably monoclonal antibodies directed against the mutant FGFR3. Polyclonal antibodies and modified polyclonal antibodies may also be used however.

Monoclonal antibodies produced against the receptor can be produced by biologically pure cell lines of immon talized antibody-producing cells. Immortalized antibody producing cells can be obtained according to any of the various methods which are known in the art, and generally include the steps: 1) inducing suitable cells such as lymphocytes to produce specific antibodies (for example, by injecting an immunogen such as the polypeptide of SEQ ID NO:2, wherein Xaa at position 23 is a polar amino acid such as glutamic acid), 2) immortalizing those cells, and 3) selecting clones out of those cells which produce antibodies of the desired specificity and affinity. For example, one method would be that of Kohler and Millstein, *Nature,* vol. 256, 495–497 (1975). This method involves immunizing mice with the particular peptide (e.g., that of SEQ ID NO:1), isolating spleen cells and fusing them with mouse myeloma cells to obtain hybridomas. Of course, animals other than mice could be used as well.

Monoclonal antibodies with affinities of $10^{-8}$ $M^{-1}$ or preferably $10^{-9}$ $M^{-1}$ to $10^{-10}$ $M^{-1}$ or stronger will typically be made by standard procedures as described. See, e.g., Harlow & Line, *Antibodies: A Laboratory Manual* (Cold Spring Harbor Laboratory, Cold Spring Harbor, N.Y., US, 1988), Goding, *Monoclonal Antibodies: Principles and Practice* (2d ed., Academic Press, NY, US, 1986).

Other suitable techniques to make antibodies involve in vitro exposure of lymphocytes to the antigenic polypeptides (such as the polypeptide of SEQ ID NO:1 or an antigenic component thereof), or, alternatively, to selection of antibodies in phage or similar vectors. See, Huse et al. *Science,* 246:1275–1281 (1989). Also, recombinant immunoglobulins may be produced. See, U.S. Pat. No. 4,816,567.

The peptides and antibodies of the present invention may be used with or without modification. Often, peptides and antibodies are labeled by joining, covalently or non-covalently, a substance which provides for a detectable signal. A wide variety of labels and conjugation techniques are known in the art, and are reported extensively in both the scientific and patent literature. Suitable labels include radiolabels, enzymes, substrates, co-factors, inhibitors, fluorescent agents, chemiluminescent agents, magnetic particles and so forth. See, e.g., U.S. Pat. Nos. 3,817,837, 3,850,752, 3,939,350, 3,996,345, 4,277,437, 4,275,149, and 4,366,241.

Polyclonal antibodies may be produced by selecting an appropriate target immune system such as that of a mouse, sheep or rabbit. Substantially purified antigen is presented to the selected immune system in a fashion determined by methods appropriate for the animal and by other parameters well known to immunologists. Typical sites for injection are in the footpads, intramuscularly, intraperitoneally, or intradermally. Of course, other species may be substituted for mouse, rabbit or sheep. Polyclonal antibodies are then purified using techniques known in the art, adjusted for the desired specificity.

Antigens, such as the polypeptide of SEQ ID NO:1, may be purified by various methods. For instance, methods for isolating a polypeptide from other biological material, such as from cells transformed with the recombinant nucleic acids encoding a FGFR3, include immuno-affinity chromatography employing, for example, the antibodies provided by the instant invention. Various methods of protein purification are well known in the art. See, e.g., Deutscher *Meth.Enzymology,* 182 (Academic Press, San Diego, Calif., US 1990) and *Scopes Protein Purification: Principles and Practice* (Springer-Vertag, NY, US 1982).

E. Kits

The invention also provides kits for detecting in an analyte a polynucleotide comprising a portion of the SLS or mutant FGFR3 locus, the kits comprising a polynucleotide complementary to the portion of the SLS locus packaged in a suitable container, and instructions for use.

In order to detect the presence of a FGFR3 allele predisposing a mammal to a disease state, for example a sheep to SLS, a biological sample such as blood is prepared and analyzed for the presence or absence of susceptibility alleles of FGFR3. Results of these tests and interpretive information may be returned to the owner or the veterinarian for communication to the owner of the tested mammal. Such diagnoses may be performed by diagnostic laboratories, or, alternatively, diagnostic kits are manufactured and sold to, for example, veterinarians or shepherds.

Initially, the screening method involves amplification of the relevant FGFR3 sequences. In another preferred embodiment of the invention, the screening method involves a non-PCR based strategy. Such screening methods include methodologies that are well known in the art. Both PCR and non-PCR based screening strategies can detect target sequences with a high level of sensitivity. Presently, the most popular method appears to be target amplification. Here, the target nucleic acid sequence is amplified with polymerases. One particularly preferred method using polymerase-driven amplification is PCR. The polymerase chain reaction and other polymerase-driven amplification assays can achieve over a million-fold increase in copy number through the use of polymerase-driven amplification cycles. Once amplified, the resulting nucleic acid can be sequenced, cut with restriction enzymes, and/or separated by size using, for example, electrophoresis, or used as a substrate for DNA probes.

The biological sample to be analyzed, such as blood or serum, may be treated, if desired, to extract the nucleic acids. The sample nucleic acid may be prepared in various ways to facilitate detection of the target sequence; for example, denaturation, restriction digestion, electrophoresis or dot blotting.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region, for example, ovine chromosome 6. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al. *Molecular Cloning: A Laboratory Manual* (Cold Spring Harbor Laboratory, Cold Spring Harbor, N.Y., US, 1982) and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, for example., Matthews & Kricka, *Anal. Biochem.,* 169:1 (1988); Landegren et al. *Science,* 242:229 (1988); Mittlin, *Clinical Chem.,* 35:1819 (1989); U.S. Pat. No. 4,868,105, and in European Patent Office Publication No. 225,807.

As previously noted, non-PCR based screening assays are also contemplated in this invention. One such procedure hybridizes a nucleic acid probe (or an analog such as a methylphosphonate backbone replacing the normal phosphodiester), to the low level DNA target. This probe may have an enzyme covalently linked to the probe, such that the covalent linkage does not interfere with the specificity of the hybridization. This enzyme-probe-conjugatetaget nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al. *Nuc. Acids Res.,* 14:6115–6128 (1986).

Other methods such as PCR, oligohybridization, and direct sequencing might be used. These methods are well known to those of skill in the art.

Two-step label amplification methodologies are known in the art. These assays work on the principle that a small ligand (such as digoxigenin, biotin, or the like) is attached to a nucleic acid probe capable of specifically binding FGFR3. Exemplary probes are provided in this patent application and include the nucleic acid probes derived from SEQ ID NO:1. Allele specific probes are also contemplated within the scope of this invention.

In one case, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment. See Martin et al. *BioTechniques,* 9:762–768 (1990). In another case, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al. *J. Mol. Biol.,* 113:237–251 (1977) and Nguyen et al. *BioTechniques,* 13:226–23 (1992).

It is also contemplate within the scope of this invention that the nucleic acid probe assays of this invention will employ a cocktail of nucleic acid probes capable of detecting FGPR3. Thus, in one example to detect the presence of FGFR3 in a cell sample, more than one probe complementary to FGFR3 is employed and in particular the number of different probes is alternatively 2, 3, or 5 different nucleic acid probe sequences. In another example, to detect the presence of mutations in the FGFR3 gene sequence in a subject animal, more than one probe complementary to FGFR3 is employed where the cocktail includes probes capable of binding to the allele-specific mutations identified in populations with alterations in FGFR3. In this embodiment, any number of probes can be used, and will preferably include probes corresponding to the major gene mutations identified as predisposing a subject to a disease state.

Preferred embodiments relating to methods for detecting FGFR3 or its mutations include enzyme linked immunosorbent assays ("ELISA"), radioimmunoassays ("RIA"), immunoradiometric assays ("IRMA") and immunoenzymatic assays ("IEMA"), including sandwich assays using monoclonal and/or polyclonal antibodies. Exemplary sandwich assays are described by David et al. in U.S. Pat. No. 4,376,110 and 4,486,530, hereby incorporated by reference.

F. Gene Therapy

The implications of the invention with respect to gene therapy will generally take the form of therapeutic agents having polynucleotides coding for all or a portion of the correct FGFR3 gene placed in appropriate vectors or delivered to target cells in more direct ways such that the proper function of FGFR3 is restored or reconstituted.

Alternatively, the discovery that the herein described glutamic acid for valine substitution in FGFR3 leads to, among other things, taller individuals may be useful in the treatment of dwarfism in a mammal (e.g., a human). In such a situation, gene therapy techniques may be used to counteract the mutations of dwarfism. In other words, the dwarfism mutations in FGFR3 cause the gene to "over regulate", shutting off bone growth at an inappropriately early stage of development. In Spiders, the mutant form causes the gene to "under regulate", not stopping bone growth at the appropriate stage. By inserting an FGFR3 gene containing the spider mutation into cells expressing the dwarfism form of the FGFR3 gene, it may be possible to counteract the effects, resulting in a more normal phenotype.

According to this aspect of the present invention, a method is also provided of supplying wild-type FGFR3 function to a cell which carries mutant FGFR3 alleles. Supplying such a function should encourage proper expression of FGFR3 and alleviate the symptoms of, for example, SLS. The wild-type FGFR3 gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant FGFR3 allele, the gene fragment should encode the proper FGFR3 protein. More preferred is the situation where the wild-type FGFR3 gene or a part thereof is introduced into the mutant cell in such a way that it recombines with the endogenous mutant FGFR3 gene present in the cell. Such recombination requires a double recombination event which results in the correction of the FGFR3 gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the routineer. Cells transformed with the wild-type FGFR3 gene can be used as model systems to study SLS.

As generally previously discussed, the FGFR3 gene or fragment, where applicable, may be employed in gene therapy methods in order to increase the amount of the expression products of such genes in the appropriate cells.

Gene therapy would be carried out according to generally accepted methods. A virus or plasmid vector containing a copy of the FGFR3 gene linked to expression control elements and capable of replicating inside embryo cells is prepared. Suitable vectors are known. The vector is then incorporated into the embryo. If the transfected gene is not permanently incorporated into the genome of each of the targeted cells, the treatment may have to be repeated periodically.

Gene transfer systems known in the art may be useful in the practice of the gene therapy methods of the present invention. These include viral and non-viral transfer methods. A number of viruses have been used as gene transfer vectors with various mammals, including papovaviruses, adenovirus, vaccinia virus, adeno-associated virus, herpesviruses including HSV and EBV, and retroviruses of avian, murine, and human origin. Some gene therapy protocols have been based on disabled murine retroviruses.

Non-viral gene transfer methods known in the art include chemical techniques such as calcium phosphate co-precipitation (Pellicer et al. *Science*, 209:1414–1422 (1980)); mechanical techniques, for example microinjection (Brinster et al. *Cell*, 27:223–231 (1981)); membrane fusion-mediated transfer via liposomes (Stewart et al. *Hum. Gen. Ther.*, 3:267–275 (1992)); and direct DNA uptake and receptor-mediated DNA transfer. Viral-mediated gene transfer can be combined with direct in vivo gene transfer using liposome delivery, allowing one to direct the viral vectors to the tumor cells and not into the surrounding nondividing cells. Alternatively, the retoviral vector producer cell line can be injected into tumor. Injection of producer cells would then provide a continuous source of vector particles.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

The invention is further explained by the following illustrative examples:

EXAMPLES

Example I

In order to identify a genetic marker for the SLS defect, a sheep flock segregating for the SLS gene was established.

During the following years, blood and/or tissue samples were collected from 59 Spider and 84 normal lambs. These lambs were the offspring of a heterozygous ram that had been mated to 52 ewes, 14 of which were his daughters.

Samples were then collected from 33 Spider and 91 normal lambs that were the offspring of a second heterozygous ram. This male was mated to 36 ewes, 15 of which were daughters of the first heterozygous ram.

In total, there were 61 ewes, including 20 daughters and the mother of the first heterozygous ram. Twenty-seven females produced lambs from both rams, 25 produced lambs from only the first heterozygous ram, and 9 produced offspring from only the second heterozygous ram. Forty-two of these ewes, including 10 the first heterozygous ram daughters, were obligate carriers of the SLS mutation in that they have produced at least one Spider lamb during the time they were in the flock.

Phenotypes for SLS were determined in the lambs based on three measurements: physical appearance, radiographs of the anconeal process and histological examination of chondrocytes in the anconeal process and the sternebrae. A lamb that showed angular limb deformities, kyphoscoliosis, Roman nose, and sternal displacement were each considered positive for physical signs of SLS. A lamb was judged to have positive radiographic signs for SLS if islands of ossification were seen around the anconeal process. A lamb exhibiting chondrodysplasia on histological examination was considered histologically positive for SLS. Lambs with two or more positive measurements were recorded as Spider, those with no positive measurements were recorded as normal, and those lambs with only one positive measurement were considered ambiguous (25/292 or 8.6%) and therefore, not included in the data set.

Example II

Genomic DNA was extracted from samples collected on all animals of Example I in the pedigrees. A genome scan using microsatellite markers was then initiated. These markers were identified based on information from existing genome maps of cattle and sheep. The markers were selected to systematically search the genome, having markers spaced about 20 centiMornans, or approximately 20 million base pairs, apart. In total, 551 markers were obtained from researchers or were commercially synthesized using published primer sequences. Of these markers, 503 (91.3%) successfully amplified ovine DNA using protocols developed in our laboratory.

The first hetemzygous ram and the second heterozygous ram rams were informative (i.e., heterozygous) for 181 (32.8%) and 234 (42.5%) of the markers, respectively.

During years two and three, the first heterozygous ram pedigree was genotyped for 38 markers. Following the year five lambing season, an additional 82 markers were completed for the second heterozygous ram pedigree. As genotypes were completed, each marker was analyzed for linkage with the SLS gene using LODSCORE™ (Lathrop et al. "Strategies for multilocus linkage analysis in humans", *Proc.Natl.Acad.Sci.* (USA), 101:3443–3446 (1984)); however, no significant linkage was identified for any of these markers. Following the birth of the year six lambs, a series of steps were undertaken with emphasis placed on the second heterozygous ram pedigree to reduce the total number of genotypes required in performing the genome scan. Previously untested markers for which the second heterozygous ram was informative (79 in total) were genotyped on a subset of his offspring including 31 Spider lambs and their dams. Resulting genotypes were entered into the data set and analyzed for linkage with SLS. Those markers with lod scores>0.15 from this analysis (12 of 79 total markers) were then genotyped on the full the second heterozygous ram pedigree. Two markers with lod scores>1.20 after analysis of the full pedigree were then tested on the first heterozygous ram pedigree.

Results from the marker OarJMP8, located on the distal end of ovine chromosome 6 (Lumsden et al. "Characterization and linkage mapping of ten sheep microsatellite markers derived from a sheep x hamster cell hybrid", *Anim. Genet.*, 27:203–206 (1996)), revealed significant linkage with the SLS gene. Analysis of the full second heterozygous ram pedigree resulted in a lod score of 1.61 at 25.6% recombination. Additionally, the first heterozygous ram pedigree analysis resulted in a lod score of 2.33 at 29.4% recombination. A final combined lod score of 3.89 at 28.1% recombination was then obtained, demonstrating significant linkage between the SLS gene and OarJMP8, with assignment of the SLS locus to ovine chromosome 6.

Three additional markers that had been previously mapped to this region have also been linked to SLS. These markers include McM214 (Hulme et al. "Polymorphic sheep microsatellites at the McM2, McM131, McM135, McM136, McM140, McM200, McM214, McM373, McM50S, McM507 and McM512 loci", *Anim. Genet.*, 26:369–370 (1995); Maddox et al. "Updating the sheep linkage map", *Anim. Genet.*, 27(Suppl. 2):85–86 (1996)), BL1038 (Kappes et al. "A Second-Generation Linkage Map of the Bovine Genome", *Genome Research*, 7:235–249 (1997)) and OarJMP12 (Lumsden et al., 1996). A maximum lod score of 12.40 was obtained between the SLS locus and BL1038 at 8% recombination. Final order of the loci in this region was determined as OarJMT8-McM214-OarJMP1 2-BL1 038-SLS, with recombination frequencies of 6%, 7%, 2% and 8%, respectively. This order was $2.54 \times 10^{21}$ times more likely than placement of SLS in the adjacent OarJMP12-BL1038 interval.

Several additional markers previously mapped to ovine chromosome 6 have also been analyzed in these pedigrees; however, no significant linkage with SLS was detected with any of these other markers. A linkage map incorporating all of the information for ovine chromosome 6 is presented in FIG. 1.

Example III

A comparative mapping approach was initiated to identify candidate genes that are located on ovine chromosome 6 (OAR6). Prior mapping of structural genes on OAR6 indicates that it is orthologous to human chromosome 4 (HSA4; Lord et al, 1996). Furthermore, examination of the genetic linkage map of OAR6 shows that distal to the microsatellite markers OarJMP8 and OarJMP12 are genes mapping within HSA4p16.3 (Lord et al. "The linkage map of sheep chromosome 6 compared with orthologous regions in other species", *Mammal. Genome*, 7:373–376 (1996); Weber et al. "Genomic organization and complete sequence of the human gene encoding the beta-subunit of the cGMP phosphodiesterase and its localization to 4p16.3", *Nucl. Acids Res.*, 19:6263–6268 (1991)).

Contained within HSA4p16.3 is the gene for fibroblast growth factor receptor 3 (FGFR3; Thompson et al. "A gene encoding a fibroblast growth factor receptor isolated from the Huntington disease gene region of human chromosome 4", *Genomics*, 11:1133–1142 (1991)). Mutations in the FGFR3 gene of humans result in several skeletal deformities of varying phenotypes including achondroplasia (Shiang et al. "Mutations in the transmembrane domain of FGFR3 cause the most common genetic form of dwarfism, achondroplasia", *Cell*, 78:335–342 (1994)), hypochondroplasia (Bellus et al., "A recurrent mutation in the tyrosine kinase domain of fibroblast growth factor receptor 3 causes hypochondroplasia", *Nature Genet.*, 10:357–359 (1995)) and thanatophoric dysplasia (Tavormina et al. "Thanatophoric dysplasia (types I and II) caused by distinct mutations in fibroblast growth factor receptor 3", *Nature Genet*, 9:321–328 (1995)). Most recently, two groups have produced mice in which the FGFR3 gene is disrupted by homologous recombination (Colvin et al. "Skeletal overgrowth and deafness in mice lacking fibroblast growth factor receptor 3", *Nature Genetics*, 12:390–397 (1996); Deng et al. "Fibroblast growth factor receptor 3 is a negative regulator of bone growth", *Cell*, 84:911–921 (1996)). Remarkably, mice homozygous for the FGFR3 knockout display skeletal abnormalities that are reminiscent of Spider Lamb Syndrome. These abnormalities include exaggerated skeletal growth, severe scoliosis and kyphosis. From these knockout studies, the function of FGFR3 can be defined as a negative regulator of bone growth. This is in agreement with recent studies that find FGFR3 to be constitutively activated in the various human diseases resulting suppression (i.e., overregulation) of bone growth (Naski et al. "Graded activation of fibroblast growth factor receptor 3 by mutations causing achondroplasia and thanatophoric dysplasia", *Nature Genetics* 13:233–237 (1996); Webster et al. "Constitutive activation of fibroblast growth factor receptor 3 by the transmembrane domain point mutation found in achondroplasia", *EMBO J*, 15:520–527 (1996)).

To investigate whether ovine FGFR3 may be the causative defect in SLS, oligonucleotide primers were designed from the human and mouse orthologs. Of the three sets of primers used, one set resulted in the successful amplification of a 953 base pairs fragment containing the 3' end of exon 14, exons 15–17, and the 5'-end of exon 18 of the FGFR3 gene. The fragment was digested with several restriction enzymes and analyzed using a SSCP analysis. Two SSCPs were identified, one of which appeared to be predictive of SLS genotype (FIG. 2).

Example IV

Figure 2:
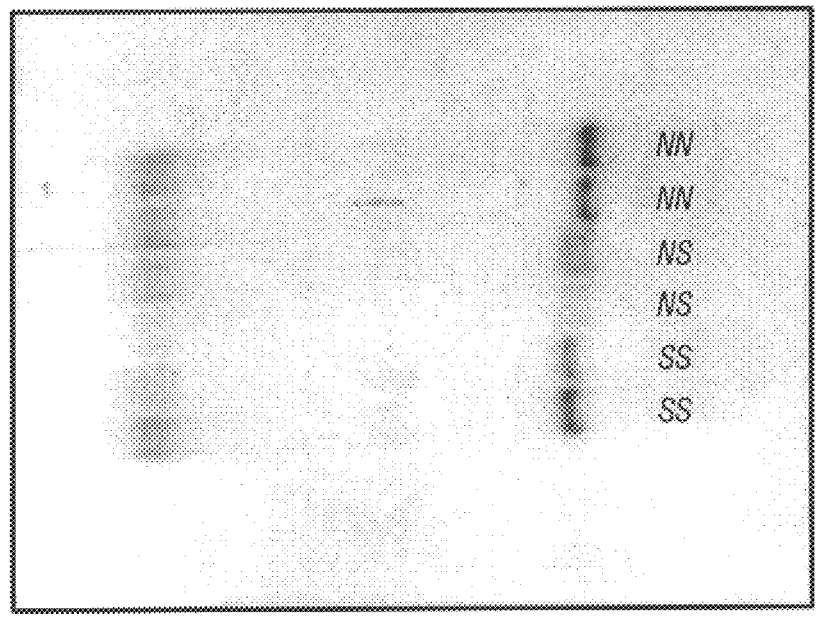
FIG. 2 is a gel depicting a single strand conformational polymorphism in a 413 base pair HhaI fragment of the ovine fibroblast growth factor receptor 3 gene. Included on the gel are two homozygous normal ("NN"), two heterozygous ("NS"), and two Spider ("SS") animals.

The SSCP of FIG. 2 has been typed in a subset of the first heterozygous ram and the second heterozygous ram pedigrees. In total, 88 normal and 47 Spider lambs and their parents were included in the linkage analysis, resulting in a lod score of 18.58 at 0% A recombination. Further investigation of this SSCP was then conducted. Genomic DNA from one homozygous normal animal (a white-faced Rambouillet male), two carriers (the second hetemzygous ram and an obligate female) and two Spider lambs was amplified and sequenced. Analysis of the sequence revealed a T→A transversion in exon 17, resulting in a non-conservative amino acid substitution of Val→Glu at amino acid position 700 found within the second tyrosine kinase domain (FIG. 3). Note: The mutation at amino acid position 700 corresponds to nucleotide position 2099; this numbering is based on the proposed start codon of the human FGFR3 mRNA.

To detect this nucleotide transversion, a polymerase chain reaction-restriction fragment polymophism (PCR-RFLP) was developed. Primer sequences were designed to flank the mutation described above and amplify a DNA fragment of 147 base pairs (bp). The 5' primer sequence was modified from the original ovine sequence to incorporate an XhoI recognition site and this prinmer is immediately adjacent to the mutation. The presence of A (the spider allele) at nucleotide position 2099 will result in cleavage by XhoI. "Spider allele" or "Spider Lamb Syndrome allele" refers to alleles carrying variations that are causative or predisposing for SLS. The presence of T (the normal allele) at nucleotide position 2099 will prevent cleavage by XhoI. The 3' primer sequence was also modified to incorporate a second XhoI site, completely within the primer sequence and therefore, this site is present in all PCR products and provides a "positive" control for XhoI cleavage. 5' and 3' primer sequences for use within PCR-RFLP of the ovine FGFR3 gene, with XhoI recognition sites underlined, are:
5' sequence

```
Original
Sequence       (SEQ.ID.NO:3)   TCGCCGTACCCTGGCATCCCCG
                                         |             |
Modifications  (SEQ.ID.NO:4)   TCGACGTACCCTGGCATCCTCG
```

3' sequence:

```
Original
Sequence       (SEQ.ID.NO:5)   CCAGCGCCCGGCCCTCGGGACT
                                         |             |
Modifications  (SEQ.ID.NO:6)   TCAGCGCCCGGCCCTCGAGACT
```

Figure 4:
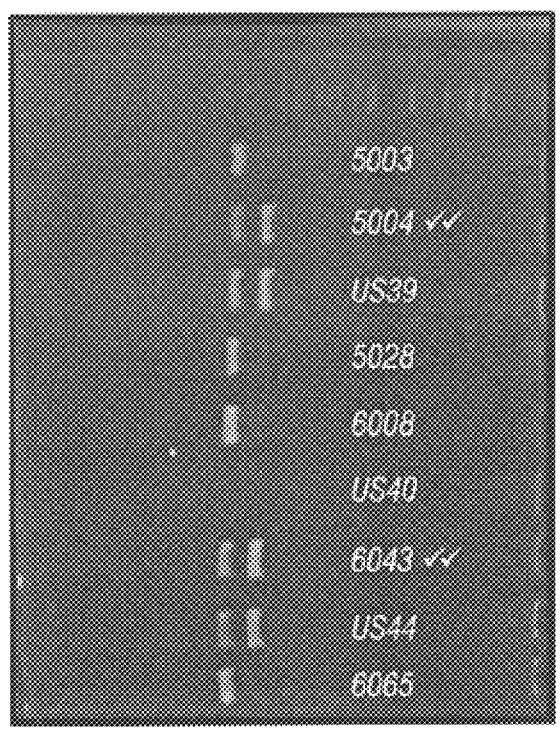
FIG. 4 depicts a PCR-RFLP in a 147 base pair fragment of the ovine FGFR3 gene showing the 132 (top) and 112 base pair fragments.
Figure 5:
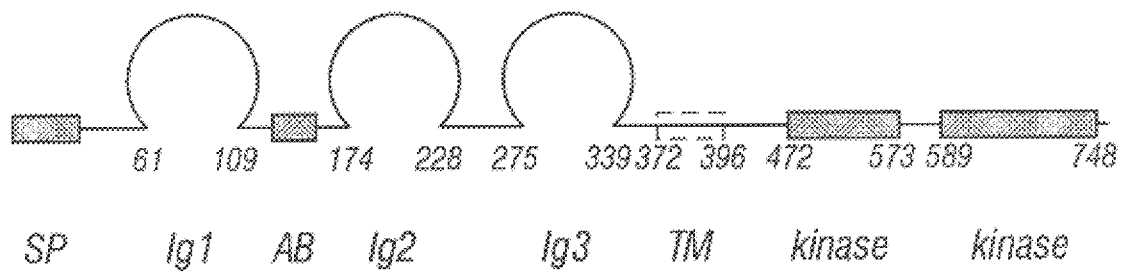
FIG. 5 graphically depicts a map of the FGFR3 gene illustrating the gene's various introns and functional domains.

Thus, the 147 base pairs fragment is cleaved into two fragments (132 bp and 15 bp fragments) within the normal allele. The 132 base pairs fragment is further cleaved into two fragments (112 bp and 20 bp) within the Spider allele. In conducting PCR-RFLP analysis (see above), the homozygous normal animals are defined by the presence of only the 132 base pairs fragment, homozygous spider animals are defined by the presence of only the 112 base pairs fragment, and heterozygous animals are defined by the presence of both the 132 and 112 base pairs fragments (FIG. 4).

Example V

The previously described PCR-RFLP procedure was used to confirm that the FGFR3 was causative of SLS with the following results:

| Classification | NN | NS | SS | Accuracy |
| --- | --- | --- | --- | --- |
| White | 194 | 0 | 0 | 100% |
| Carrier | 0 | 174 | 0 | 100% |
| Spider | 0 | 6 | 175 | 97% |
| Grey | | >1800 | 0 | |

Included are homozygous normal ("NN"), heterozygous ("NS"), and Spider ("SS") animals based on the genetic testing. White animals are those from blood lines that have never produced spider lambs. Carrier animals are those that are normal in appearance but have produced at least one spider lamb. Spider animals are those demonstrating typical characteristics of a spider lamb. Grey animals are those that are normal in appearance and are from blood lines that have produced spider lambs.

It is believed that the 6 spider animals which tested as NS are exceptions to the autosomal recessive mode of inheritance. Sometimes in certain genetic backgrounds even one copy of the mutant FGFR3 gene would be enough to cause the Spider characteristics. It is not believed that these cxceptiolls suggest a discrepancy in the test, as all other categories including over 2000 animals are predicted accurately.

Example VI

Genetic markers and linkage analysis. Microsatellite markers were identified from existing genome maps of both sheep and cattle (Bishop et al. "A genetic linkage map for cattle", *Genetics* 136, 619–639 (1994); Crawford et al. "An autosomal genetic linkage map of the sheep genome", *Genetics* 140:703–724 (1995)) and were selected to maximize genome coverage with marker spacing between 10 and 20 centiMorgans (cM). Two-point linkage analysis was performed sequentially for each marker using FASTLINK (Lathrop et al. 1984; Cotfingham et al. "Faster sequential genetic linkage computations", *Amer J Human Genet,* 53, 252–263 (1994); Schaffer et al. "Avoiding recomputation in linkage anlaysis", *Human Hered,* 44, 225–237 (1994) or the TWOPOINT option of CRI-MAP (version 2.4; Green et al. *Documentation of CRI-MAP,* version 2.4. (St. Louis, Washington University School of Medicine) 1990). Multipoint linkage maps were constructed using BUILD and locus order probabilities calculated using FLIPS (Green et al. 1990). When using CRI-MAP, obligate carriers were recorded as heterozygotes whereas the genotypes of the remaining ewes were not assigned. Assuming complete penetrance, Spider lambs were recorded as homozygous. Inbreeding loops were broken to facilitate the linkage analysis.

Single-strand conformation polymorphism (SSCP) analysis. Oligonucleotide primers for the amplification of ovine fibroblast growth factor receptor 3 were designed based on the comparison of human and mouse sequences (Genbank #M58051 and #M81342). Primer sequences corresponding to nucleotides 1689 to 1709 (SEQ ID NO:7) (5'-CCTGTACGTGCTGGTGGAGTA-3') and 2270 to 2249 (SEQ ID NO:8) (5'-AGCTGCTMGAAGGTGGGCCTCT-3') of the human cDNA sequence were used to amplify ovine FGFR3. Amplification was performed in a 10 $\mu$pl volume containing 1×PCR buffer (50 mM KCl; 10 mM Tris, pH 8.3; 1.5 mM MgCl$_2$), 100 $\mu$M of each dNTP, 1 $\mu$Ci [$\alpha$-$^{32}$P]-dCTP (3000 $\mu$Ci mmole$^{-1}$), 0.5 U Amplitaq DNA polymerase, 0.5 $\mu$M of each primer and 30 ng of genomic DNA. Reactions were incubated at 94° C. for 4 min followed by 32 cycles of 94° C. for 1 min., 62° C. for 1 min., and 72° C. for 1 min., and a final incubation at 72° C. for 5 min. Following amplification, PCR products were digested by the addition of a 5 $\mu$l volume containing 1.5 $\mu$l of 1OX digestion buffer and 5 U of Hha I and incubated at 37° C. for 3 hr. The resulting fragments were subjected to SSCP analysis according to methods described by Beever and coworkers (1997).

Results

A total of 551 microsatellite markers was obtained from researchers or commercially synthesized using published primer sequences. Of these markers, 503 (91.3%) were successfully amplified from ovine DNA. Genotypes were obtained for both rams used in the project; ram 1 was heterozygous for 181 (36.0%) markers and ram 2 heterozygous at 234 (46.5%) loci. During years 2 and 3, pedigree 1 was genotyped for 38 markers and following the year 5 lambing season, pedigree 2 was genotyped for 82 markers. However, linkage was not detected between SLS and any marker.

In year 6, emphasis was placed on pedigree 2 to reduce the total number of genotypes required in performing the genome scan. Seventy-nine previously untested markers for which ram 2 was heterozygous were genotyped on a subset of his offspring including 31 Spider lambs and their dams. Markers with a LOD score greater than 0.15 (n=12) were then genotyped on the remainder of pedigree 2. Of the 12 markers, a linkage statistic of 1.61 was obtained for the marker OarJMP8 that was subsequently genotyped for pedigree 1. A combined LOD score of 2.85 with a corresponding recombination frequency ($\theta$) of 28.1% was obtained with both pedigrees (Table 1).

TABLE 1

Pairwise recombination frequencies and maximum LOD scores for telomeric ovine chromosome 6 loci and Spider Lamb Syndrome (SLS)[1].

|  | BM4311 | CSRD293 | OarJMP8 | McM214 | OarJMP12 | BL1038 | FGFR3 | SLS |
|---|---|---|---|---|---|---|---|---|
| BM4311 |  | 0.07 | 0.13 | 0.17 | 0.24 | 0.33 | —[2] | 0.39 |
| CSRD295 | 38.19 |  | 0.06 | 0.10 | 0.16 | 0.21 | 0.34 | 0.42 |
| OarJMP8 | 24.53 | 41.71 |  | 0.05 | 0.14 | 0.17 | 0.27 | 0.28 |
| McM214 | 3.19 | 7.00 | 22.18 |  | 0.05 | 0.06 | 0.00 | 0.03 |
| OarJMP12 | 1.92 | 5.03 | 29.58 | 29.56 |  | 0.01 | 0.08 | 0.03 |
| BL1038 | 0.18 | 2.28 | 20.31 | 19.73 | 71.95 |  | 0.04 | 0.03 |
| FGFB310 | — | 0.38 | 2.41 | 4.52 | 6.91 | 9.07 |  | 0.00 |
| SLS | 0.10 | 0.02 | 2.85 | 4.62 | 13.47 | 12.89 | 13.25 |  |

[1]Recombination frequencies are given above the diagonal with corresponding LOD scores below the diagonal. Linkage statistics were calculated using the TWOPOINT option of CRI-MAP.
[2](–) indicates that markers were unlinked in this analysis.

Example VI
Monoclonal Antibodies Directed against Mutant FGFR3

Monoclonal antibodies are generated according to the following protocol. Mice are immunized with immunogen comprising intact FGFR3 or FGFR3 mutant peptides conjugated to keyhole limpet hemocyanin using glutaraldehyde or EDC as is well known.

The immunogen is mixed with an adjuvant. Each mouse receives four injections of 10 to 100 mu g of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2\times10^5$ cells/well in 96 well tissue culture plates. Individual wells are examined for growth and the supernatants of wells with growth are tested for the presence of FGPR3 specific antibodies by ELISA or RIA using wild type or mutant FGPR3 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

References

Chellaiah et al. "Fibroblast growth factor receptor (FGFR) 3: alternative splicing in immunoglobulin-like domain III creates a receptor highly specific for acidic FGF/FGF-1", *J. of Biol. Chem.*, 269:11620–11627 (1994).

Keegan et al. "Isolation of an additional member of the fibroblast growth factor receptor family, FGFR-3", *Proc. Natl.Acad.Sci.* (*USA*), 88:1095–1099 (1991).

Miller et al."A simple salting out procedure for extracting DNA from human nucleated cells", *Nucl. Acids Res.* 16:1215 (1988).

Mohammadi et al. "Identification of six novel autophosphorylation sites on fibroblast growth factor receptor 1 and elucidation of their importance in receptor activation and signal transduction", *Molec. Cell. Biol.,* 16:977–989 (1996).

Olwin et al. "Fibroblast growth factor receptor decrease during chick embryogenesis", *J. Cell Biol.,* 110:503–509 (1990).

Perez-Castro et al. "Genomic organization of the mouse fibroblast growth factor receptor 3 (Fgfr3) gene", *Genomics* 30:157–162 (1995).

Peters et al. "Unique expression pattern of the FGF receptor 3 gene during mouse organogenesis", *Devel. Biol.,* 155:423–430 (1993).

Wang et al. "A natural kinase-deficient variant of the fibroblast growth factor receptor 1", *Biochemistry,* 35:10134–10142 (1996).

Weber et al. "Genomic organization and complete sequence of the human gene encoding the beta-subunit of the cGMP phosphodiesterase and its localization to 4p16.3", *Nucl. Acids Res.,* 19:6263–6268 (1991).

Webster et al. "sConstitutive activation of fibroblast growth factor receptor 3 by the transmembrane domain point mutation found in achondroplasia", *EMBO J.,* 15:520–527 (1996).

Although the invention has been described with regard to certain preferred embodiments and illustrative examples, the scope of the invention is to be defined by the appended claims.

What is claimed is:

1. A method of identify a genetic marker for Spider Lamb Syndrome in a sheep, said method comprising:
   obtaining a sample of DNA from said sheep; and
   analyzing said sample DNA, with an oligonucleotide probe, to determine the presence or absence pf a polymorphism in a fibroblast growth factor receptor 3 (FGFR3) gene, said oligonucleotide probes being of a sufficient length to ensure specific hybridization of the oligonucleotide probe to the polymorphism region of said fibroblast growth factor receptor 3 gene.

2. The method according to claim 1 wherein the analysis of the sample of DNA to determine the presence or absence of a polymorphism is conducted as a polymerase chain reaction restriction fragment length polymorphism.

3. The method according to claim 1 wherein the analysis of the sample of DNA to determine the presence or absence of a polymorphism is conducted as single stranded conformational polymorphisms.

4. The method according to claim 1 wherein the analysis of the sample of DNA to determine the presence or absence of a polymorphism is conducted as single stranded conformational polymorphisms and as a polymerase chain reaction restriction fragment length polymorphism.

5. The method according to claim 1 wherein the analysis of the sample of DNA to determine the presence or absence of a polymorphism is conducted as a biological assay to determine the presence in said sample of mutant fibroblast growth factor receptor 3 gene having a nucleotide mutation of T1719 to A1719 in the DNA sequence of SEQ ID NO:10.

6. The method according to claim 5 wherein said biological assay comprises a DNA hybridization assay in which a labeled DNA probe is used, said probe having a sequence of at least 20 consecutive nucleotides of the DNA sequence of SEQ ID NO:10 and containing either the T1719 or A1719 nucleotide.

7. A method of performing a nucleotide amplification reaction using a DNA sample from sheep and a pair of single stranded oligonucleotide primers for determining all or part of a nucleotide sequence of a Spider Lamb Syndrome gene, said primers being selected from a sequence set forth in SEQ ID No:1.

8. A method for identifying a mutant fibroblast growth factor receptor 3 gene sequence in a sheep suspected of comprising a mutant Spider Lamb Syndrome allele, said method comprising:

comparing the nucleotide sequence of the suspected mutant Spider Lamb Syndrome allele with sheep wild-type fibroblast growth factor receptor 3 gene sequence, wherein a difference between the suspected mutant and the wild-type sequence identifies a mutant fibroblast growth factor receptor 3 gene sequence.

9. A method for screening a sheep to determine if said sheep carries the gene for Spider Lamb Syndrome, said method comprising:

providing a biological sample which was removed from said sheep to be screened and;

conducting a biological assay to determine the presence in said sample of mutant fibroblast growth factor reeptor 3 gene having a nucleotide mutation of T1719 to A1719 in the DNA sequence of SEQ ID NO:10.

10. The method according to claim 9 wherein biological assay comprises a DNA hybridization assay in which a labeled DNA probe is used, said probe having a sequence of at least 20 consecutive nucleotides of the DNA sequence of SEQ ID NO:10 and containing either the T1719 or A1719 nuclotide.

11. An isolated nucleotide sequence having at most 138 nucleotides selected from the group of sequences consisting of the sequence set forth in SEQ ID NO: 3, the sequence set forth in SEQ ID NO: 4, the sequence set forth in SEQ ID NO: 5, and the sequence set forth in SEQ ID NO: 6.

12. The isolated nucleotide sequence of claim 11 wherein the isolated nucleic acid sequence is the sequence set forth in SEQ ID NO:3.

13. The isolated nucleotide sequence of claim 11 wherein the isolated nucleic acid sequence is the sequence set forth in SEQ ID NO:4.

14. The isolated nucleotide sequence of claim 11 wherein the isolated nucleic acid sequence is the sequence set forth in SEQ ID NO:5.

15. The isolated nucleotide sequence of claim 11 herein the isolated nucleic acid sequence is the sequence set forth in SEQ ID NO:6.

16. A kit for detecting mutation in a fibroblast growth factor receptor 3 gene of a sheep comprising at least one oligonucleotide primer specific for a sheep fibroblast growth factor receptor 3 gene mutation, and instructions relating to detecting mutations in the fibroblast growth factor receptor 3 gene of the sheep.

17. A kit for assaying for the presence for a FGFR3 gene in a sheep by hybridization assay techniques, said kit comprising:

oligonucleotide sequences for PCR priming of an appropriate sheep genomic sequence;

oligonucleotide probes which specifically bind to the sheep FGFR3 gene; and reagent means for detecting the hybridization of the oligonucleotide probes to the sheep FGFR3 gene; said probes and reagent means each being present in amounts effective to perform the hybridization assay.

* * * * *

SEQUENCE LISTING

<160> NUMBER OF SEQ ID NOS: 10

<210> SEQ ID NO 1
<211> LENGTH: 138
<212> TYPE: DNA
<213> ORGANISM: Sheep
<220> FEATURE:
<221> NAME/KEY: CDS
<222> LOCATION: (1)..(138)

<400> SEQUENCE: 1

```
gtg gtc ctt cgg ggt cct gct ctg gga gat ctt cac gct ggg ggg ctc      48
Val Val Leu Arg Gly Pro Ala Leu Gly Asp Leu His Ala Gly Gly Leu
 1               5                  10                  15 gcc gta ccc tgg cat ccc cga gga gga gct ctt caa gct gct gaa gga      96
Ala Val Pro Trp His Pro Arg Gly Gly Ala Leu Gln Ala Ala Glu Gly
             20                  25                  30 agg cca ccg cat gga caa gcc ggc caa ctg cac gca tga cct             138
Arg Pro Pro His Gly Gln Ala Gly Gln Leu His Ala     Pro
         35                  40                  45
```

<210> SEQ ID NO 2
<211> LENGTH: 41
<212> TYPE: PRT
<213> ORGANISM: sheep
<220> FEATURE:
<221> NAME/KEY: VARIANT
<222> LOCATION: (23)
<223> OTHER INFORMATION: Modification associated with mutant FGFR3,
      wherein modification involves substituting an amino acid other
      than valine at position 23, the substituted amino acid generally
      being a polar amino acid.

<400> SEQUENCE: 2

```
Trp Ser Phe Gly Val Leu Leu Trp Glu Ile Phe Thr Leu Gly Gly Ser
 1               5                  10                  15

Pro Tyr Pro Gly Ile Pro Xaa Glu Glu Leu Phe Lys Leu Leu Lys Glu
             20                  25                  30

Gly His Arg Met Asp Lys Pro Ala Asn
         35                  40
```

<210> SEQ ID NO 3
<211> LENGTH: 22
<212> TYPE: DNA
<213> ORGANISM: Sheep

<400> SEQUENCE: 3
tcgccgtacc ctggcatccc cg                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: probe

<400> SEQUENCE: 4
tcgacgtacc ctggcatcct cg                                              22

<210> SEQ ID NO 5
<211> LENGTH: 22
<212> TYPE: DNA
<213> ORGANISM: Sheep

-continued

```
<400> SEQUENCE: 5
ccagcgcccg gccctcggga ct                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: probe

<400> SEQUENCE: 6
tcagcgcccg gccctcgaga ct                                              22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer used
      in amplification of ovine FGFR3

<400> SEQUENCE: 7
cctgtacgtg ctggtggagt a                                               21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer used
      in amplification of ovine FGFR3

<400> SEQUENCE: 8
agctgcttga aggtgggcct ct                                              22

<210> SEQ ID NO 9
<211> LENGTH: 46
<212> TYPE: PRT
<213> ORGANISM: Sheep

<400> SEQUENCE: 9

Trp Ser Phe Gly Val Leu Leu Trp Glu Ile Phe Thr Leu Gly Gly Ser
 1               5                  10                  15

Pro Tyr Pro Gly Ile Pro Val Glu Glu Leu Phe Lys Leu Leu Lys Glu
            20                  25                  30

Gly His Arg Met Asp Lys Pro Ala Asn Cys Thr His Asp Leu
        35                  40                  45

<210> SEQ ID NO 10
<211> LENGTH: 2049
<212> TYPE: DNA
<213> ORGANISM: Sheep

<400> SEQUENCE: 10
ggtgacagac gctccatcct cgggggatga tgaagatggg gacgacgagg ctgaggacgc     60
agcaggggcc ccttactgga cgcggcccga gcggatggac aagaagctgc tagcggtgcc    120
ggccgccaac acgttcgct tccgctgccc ggctgccggc aaccccacgc catccatcac     180
ctggctgaag aacggcaagg agttccgggg cgagcaccgc atcggaggga tcaagctgcg    240
gcaccagcag tggagcctgg tcatggagag cgtggtgccc tcggaccgcg gcaactacac    300
gtgcgtcgtg gagaacaagt ttggcagaat ccagcagacc tacaccctgg acgtgctgga    360
```

-continued

```
gcgctctccg caccggccca tcctccaggc ggggctgccc gccaaccaga ccgccgtgct    420
gggcagcgac gtggagttcc actgcaaggt gtacagcgat gcccagcccc acatccagtg    480
gctcaagcac gtggaggtga acggcagcaa ggtggggccc gacggcacgc cctacgtcac    540
cgtgctcaag acggcgggcg ctaacaccac cgacaaggag ctagaggttc tgtccttgcg    600
caatgtcacc tttgaggacg cggggagta cacgtgtctg gcgggcaatt ctatcgggtt     660
ttcccatcac tctgcgtggc tggtggtgct gccagccgag gaggagctgg tggaagctgg    720
tgaggctggc agtgtgttcg cgggcgtcct cagctacggg ctgggcttcc tcctcttcat    780
cctggctgtg gccgccgtta cgctctaccg cctgcggagc cccccaaga agggcctggg    840 ctcgcccgcg gtgcacaagg tctcccgctt cccgctcaag cgacaggtgt ccttggagtc    900
cagttcatcc atgagctcca acacgccact ggtacgcatc gcccggctgt cctcgggcga    960
gggccccacc ctgccaacg tctctgagct cgagctgccc gccgacccca agtgggagct    1020
gtcccgggcc cggctgaccc tgggcaagcc tcttggggag ggctgcttcg gccaggtggt    1080
catggcagag gccattggca tcgacaagga ccgagctgcc aagcccgtca cggtggcggt    1140
gaagatgctg aaagatgacg ccacggacaa ggacttgtcg gacctggtgt ccgagatgga    1200
gatgatgaag atgatcggaa aacataagaa cattatcaac ttgctaggcg cctgcacgca    1260
gggcgggccc ctgtacgtgc tggtggagta cgcggccaag ggcaacctac gggagtacct    1320
gcgggcgcgg cggcccccag gcactgacta ctcctkcgac acctgccggc tgcccgagga    1380
gcagctcacc ttcaaagacc tggtgtcctg cgcctaccag gtggcgcggg gcatggagta    1440
cctggcctcg cagaagtgca tccataggga cctggcggcc cgcaacgtgc tggtgaccga    1500
ggacaacgtg atgaaaatcg ccgacttcgg cctggcccgt gatgtgcaca acctcgacta    1560
ctacaagaag acaacaaacg gccgcctgcc cgtgaagtgg atggcacccg aggccttgtt    1620
tgaccgcgtc tacacccacc aaagtgatgt gtggtccttc ggggtcctgc tctgggagat    1680
cttcacgctg gggggctcgc cgtaccctgg catccccgwg gaggagctct tcaagctgct    1740
gaaggaaggc caccgcatgg acaagccggc caactgcacg catgacctgt acatgatcag    1800
gcgtgagtgc tggcacgccg cgccctcgca gaggcccacc ttcaagcagc tggtggagga    1860
cctggaccgt gtgctcactg tgacttccac tgacgagtac ctggacctgt cagtgccctt    1920
cgagcagtac tcaccgggcg gccaggacac ccccagctcc ggctcctctg gggacgactc    1980
cgtgttcgct cacgacctgc tgcccccggc ccctggtagc ggaggctctc ggacgtgaag    2040
ggccactat                                                           2049
```